United States Patent

Esclar et al.

[11] Patent Number: 6,095,000
[45] Date of Patent: Aug. 1, 2000

[54] METHOD AND APPARATUS FOR TREATING SAMPLES

[75] Inventors: Dominique Esclar, Herpy l'Arlesienne; Pierre-Luis Carmona, Gagny; Franck Leitman, Tremblay en France; Gérard Braque, Mitry le Neuf; Pascal Sterle, Soisy Sous Montmorency, all of France

[73] Assignee: L'Oreal, Paris, France

[21] Appl. No.: 08/905,081

[22] Filed: Aug. 1, 1997

[30] Foreign Application Priority Data

Aug. 13, 1996 [FR] France .................... 96 10161

[51] Int. Cl.⁷ ........................................ B65B 3/14
[52] U.S. Cl. .......................................... 73/866
[58] Field of Search ............... 73/863, 866, 865.6, 73/160, 860; 141/70, 82

[56] References Cited

U.S. PATENT DOCUMENTS

| | | |
|---|---|---|
| 2,819,739 | 1/1958 | Ehrlich et al. . |
| 3,227,130 | 1/1966 | Weiskopf . |
| 3,294,101 | 12/1966 | Suzuki et al. . |
| 4,103,722 | 8/1978 | Zollinger . |
| 4,189,896 | 2/1980 | Kolbach et al. . |
| 5,476,636 | 12/1995 | Tomiita et al. ................ 73/865.5 |

FOREIGN PATENT DOCUMENTS

| | | |
|---|---|---|
| 59-043359 | 3/1984 | Japan . |
| 1268492 | 3/1972 | United Kingdom . |

*Primary Examiner*—Robert Raevis
*Attorney, Agent, or Firm*—Oliff & Berridge, PLC

[57] ABSTRACT

An apparatus and method for implementing successive treatments on samples, such as samples of fibers, in particular hair. The method is performed by applying at least one liquid followed by drying the samples. The apparatus includes a plurality of beakers each adapted to receive a sample and into which at least one treatment liquid is fed via a feeding device. The apparatus further includes a flow device for establishing a flow of drying gas in each beaker.

19 Claims, 7 Drawing Sheets

FIG_1

FIG_2

FIG_3

FIG_4

FIG_10

FIG_11

FIG_12

FIG_13

FIG_14

FIG_15

FIG_16

FIG_17

FIG_18

FIG_19

FIG_20

METHOD AND APPARATUS FOR TREATING SAMPLES

The present invention relates to treating samples, such as samples of fibers, and in particular hair.

The invention relates more particularly to treating samples by means of at least one liquid, followed by drying.

BACKGROUND OF THE INVENTION

An apparatus is known for simultaneously treating a plurality of samples by means of a liquid, the apparatus comprising a plurality of sample-carrier baskets driven helically about a vertical axis in respective vessels filled with said liquid and maintained at a desired treatment temperature by a water bath.

At the end of treatment by said liquid, the sample-carrier baskets are withdrawn from the vessels and are placed in an oven to dry the samples.

Such apparatus does not give complete satisfaction, particularly since it requires laboratory personnel to perform a large amount of handling, thereby limiting the number of experiments that can be performed in a given length of time.

Also, when it is desired to determine the effect of a hair treatment substance on hair, it is important for tests to be performed on the samples in a manner that is as representative as possible of the real action of the substance on hair of the head, which depends in particular on the conditions under which the substance is applied to the head, and the various actions performed before or after the substance is applied, e.g. shampooing and drying.

OBJECTS AND SUMMARY OF THE INVENTION

The present invention seeks to increase the experimental options that can be performed in a given period of time while making it possible to obtain experimental results that are reproducible and highly representative of treatment performed in vivo.

This is achieved by the invention providing an apparatus for implementing successive treatments on samples, such as samples of fibers, in particular hair, in which the treatment is performed by at least one liquid and by drying the samples, the apparatus comprising a plurality of beakers each adapted to receive a sample, feed means for feeding at least one treatment liquid into each beaker, and means for establishing a flow of drying gas in each beaker.

Thus, according to the invention, each sample is treated by a liquid and is dried within a single enclosure, so there is no longer any need to extract samples from the beakers in which they have been treated by the liquid in order to put them into an external oven. This reduces the number of handling operations that laboratory personnel need to perform on the samples. In addition, treatment of the samples becomes relatively easy to automate.

According to an advantageous characteristic of the invention, the apparatus further comprises a plurality of pistons associated with respective ones of said beakers, and drive means for moving said pistons within said beakers.

It is thus possible to subject the samples to a massaging action that is close to that which is performed in reality when a dye or a shampoo is applied to the hair.

The inventors have observed that when the apparatus is used for determining the fastness of a hair dye, the tests performed with the apparatus of the invention are much more representative of the real action of the liquid when tested on hair on the head than are tests performed using the above-mentioned prior art apparatus with sample-carrier baskets.

In a preferred embodiment of the invention, the apparatus comprises control means for controlling said drive means so as to control displacement of said pistons inside said beakers.

In a first mode of operation, said pistons are caused to move with reciprocating motion over a predetermined stroke so as to apply a massaging action to the samples.

In a second mode of operation, said pistons are caused to move downwards over a greater stroke so as to perform a squeezing-out action on the samples.

In a particular embodiment of the invention, each piston has at least one treatment liquid feed channel for the corresponding beaker passing therethrough. Preferably, each piston is fitted with a flap suitable for preventing treatment liquid from moving back into said feed channel when the piston moves down into the beaker.

In a particular embodiment of the invention, the bottom of each beaker is pierced by orifices and the apparatus includes means for delivering a flow of drying gas into each beaker via said orifices.

In a particular embodiment of the invention, the apparatus includes means for selectively putting said orifices into communication either with an emptying pipe or with a blower.

In a particular embodiment of the invention, said means for feeding at least one treatment liquid into each beaker comprise:

a dispenser body having a housing into which there opens out at least one feed inlet for said liquid;

a succession of liquid-collecting chambers communicating via respective inlet orifices and outlet orifices with said housing, and via respective liquid dispensing outlets with the outside, each of said outlets being provided with closure means, capable of being opened to dispense the liquid in the corresponding beaker;

respective expulsion gas feed channels associated with said chambers;

a selector member movable in said housing between a filling position and a dispensing position; and sealing means placed in said housing between the body of the dispenser and said selector member, said body and selector member being shaped and said sealing means being positioned in such a manner that when said selector member is in the filling position they define liquid passages in said housing between an outlet orifice of one chamber and an inlet orifice of the following chamber in order to force circulation of the liquid from said feed inlet for said liquid through the various chambers in succession, and when said selector member is in the dispensing position, they close said passages so as to make it possible when said closure means associated with each chamber are open, for the liquid contained within each chamber to flow out via the corresponding liquid dispensing outlet under drive from said expulsion gas.

The number of liquid-accumulating chambers for dispensing a corresponding number of quantities of treatment liquid can be relatively high, for example sixteen, without the overall cost of the apparatus being greatly increased, because in this particular embodiment there is no need to use a large number of electrically controlled valves associated with each of the liquid-collecting chambers, respectively.

The above-mentioned expulsion gas is preferably compressed air.

In a particular embodiment of the invention, said expulsion gas feed channels open out into said housing and are isolated by said sealing means when the selector member is in the filling position.

In a particular embodiment of the invention, said sealing means are carried by the selector member which is elongate in shape and can slide inside said housing.

Preferably, each expulsion gas feed orifice is situated along the path of the selector member between the inlet orifice and the outlet orifice of a liquid-collecting chamber opening out into said housing.

In a particular embodiment of the invention, said closure means are constituted by valves that open when the pressure of the liquid in the associated liquid-collecting chamber exceeds a predetermined value.

In a particular embodiment of the invention, the volume of each liquid-collecting chamber is adjustable by moving a part carrying the associated valve.

The invention also provides a method of applying successive treatments to samples of fibers, in particular hair, including both treatment by at least one liquid and drying of said samples, wherein, for each sample, both treatment by said liquid and drying are performed in the same beaker within which the sample is placed.

In a particular implementation, said method further includes the step consisting in squeezing out each sample by means of a piston being lowered into each beaker and pressing the sample against the bottom of the beaker.

In a particular implementation, the method of the invention further includes the step consisting in delivering a jet of compressed gas via a channel passing through said piston.

In a particular implementation of the method of the invention, the method also includes the steps consisting in:
  connecting in series the volumes of a succession of liquid-collecting chambers via passages formed between a dispenser body and a selector member when in a given position relative to the dispenser body, the volume of each chamber corresponding to a predetermined quantity of substance to be dispensed into a corresponding beaker or group of beakers;
  filling said chambers by causing liquid to flow from the first chamber to the last chamber, passing from one chamber to the next by overflowing;
  isolating the chambers from one another by displacing the selector member relative to the body of the dispenser to close said passages; and
  delivering expulsion gas into each chamber to enable the liquid contained therein to escape via a liquid dispensing outlet and fill the corresponding beaker or group of beakers.

BRIEF DESCRIPTION OF THE DRAWINGS

Other characteristics and advantages of the present invention appear on reading the following detailed description of a non-limiting embodiment of the invention, and on examining the accompanying drawings, in which.

DETAILED DESCRIPTION OF PREFERRED EMBODIMENTS

Figure 1:
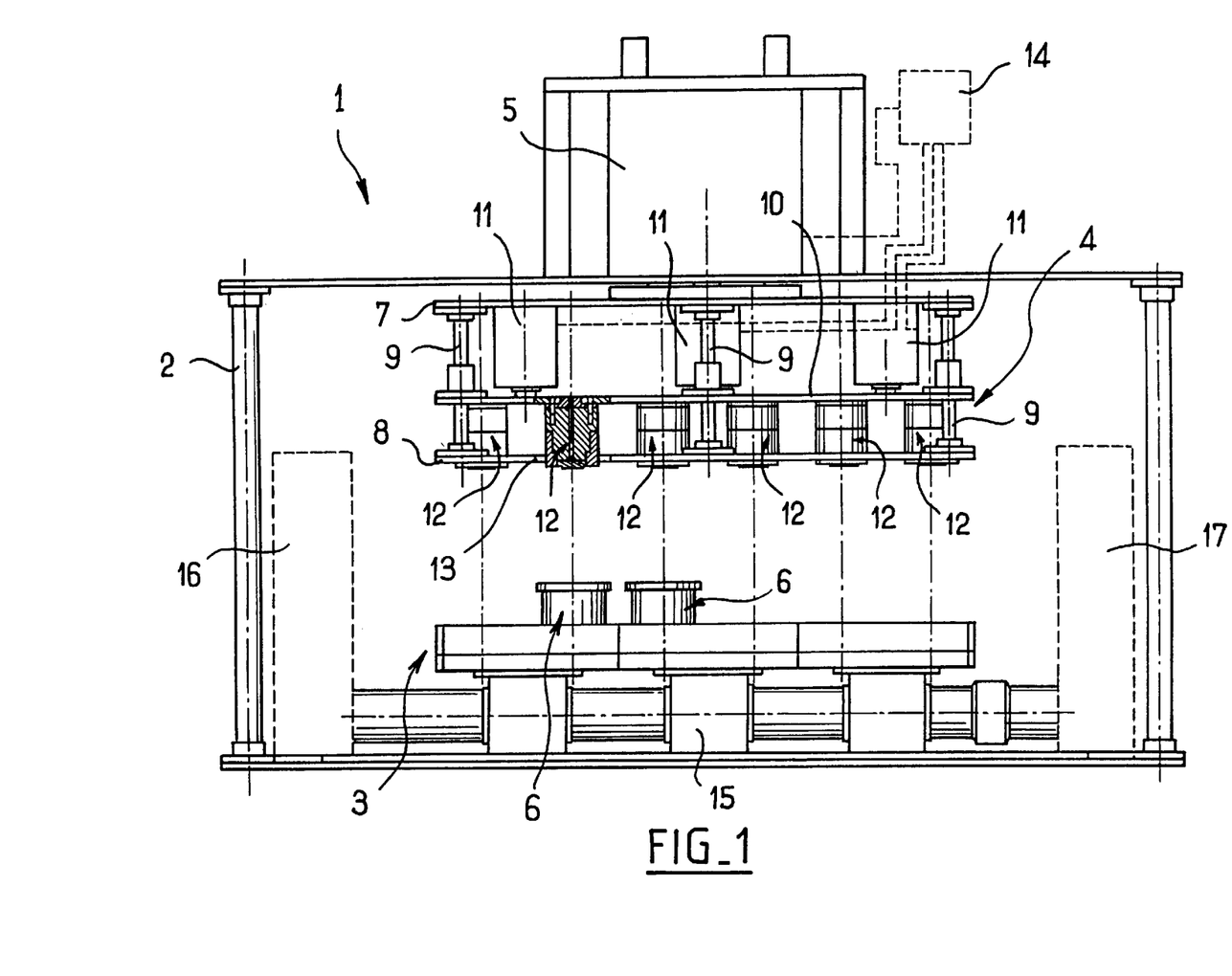
FIG. 1 is a diagrammatic front elevation view of apparatus constituting a particular embodiment of the invention.

FIG. 1 shows apparatus constituting a particular embodiment of the invention.

The apparatus 1 comprises a stand 2 serving as a support for a sample-carrier plate 3 and an assembly 4 which is suspended above the plate 3 and which is capable of sliding on vertical uprights secured to the stand 2, under drive from an actuator 5.

The plate 3 has a plurality of housings for receiving respective beakers 6 in which samples are placed for testing. In the example described, each beaker 6 is independent, however it would not go beyond the ambit of the invention to secure a plurality of beakers to one another, or indeed to make a plurality of individual treatment bowls by appropriately shaping a sheet of plastics material, for example.

The assembly 4 has top and bottom horizontal plates 7 and 8 facing each other and interconnected by vertical spacers 9. A tray 10 is slidably mounted on the spacers 9 between the plates 7 and 8 and moves under drive from actuators 11, having their bodies secured to the top plate 7.

A plurality of pistons 12, whose role is explained below, are fixed to the tray 10 and extend vertically downwards. Orifices 13 are formed through the bottom plate 8 to pass the pistons 12 when the tray 10 is lowered under drive from the actuators 11.

Control means 14, represented diagrammatically in FIG. 1, are provided to control the movement of the actuators 5 and 11 in a manner that is described below.

Each beaker 6 is connected at its bottom to a pipe 15 which serves both as an emptying pipe and as a feed pipe for delivering drying air. The pipe 15 can thus be connected either to emptying means 16 or to a blower 15, both known per se and represented very diagrammatically.

Figures 2, 3, 4:
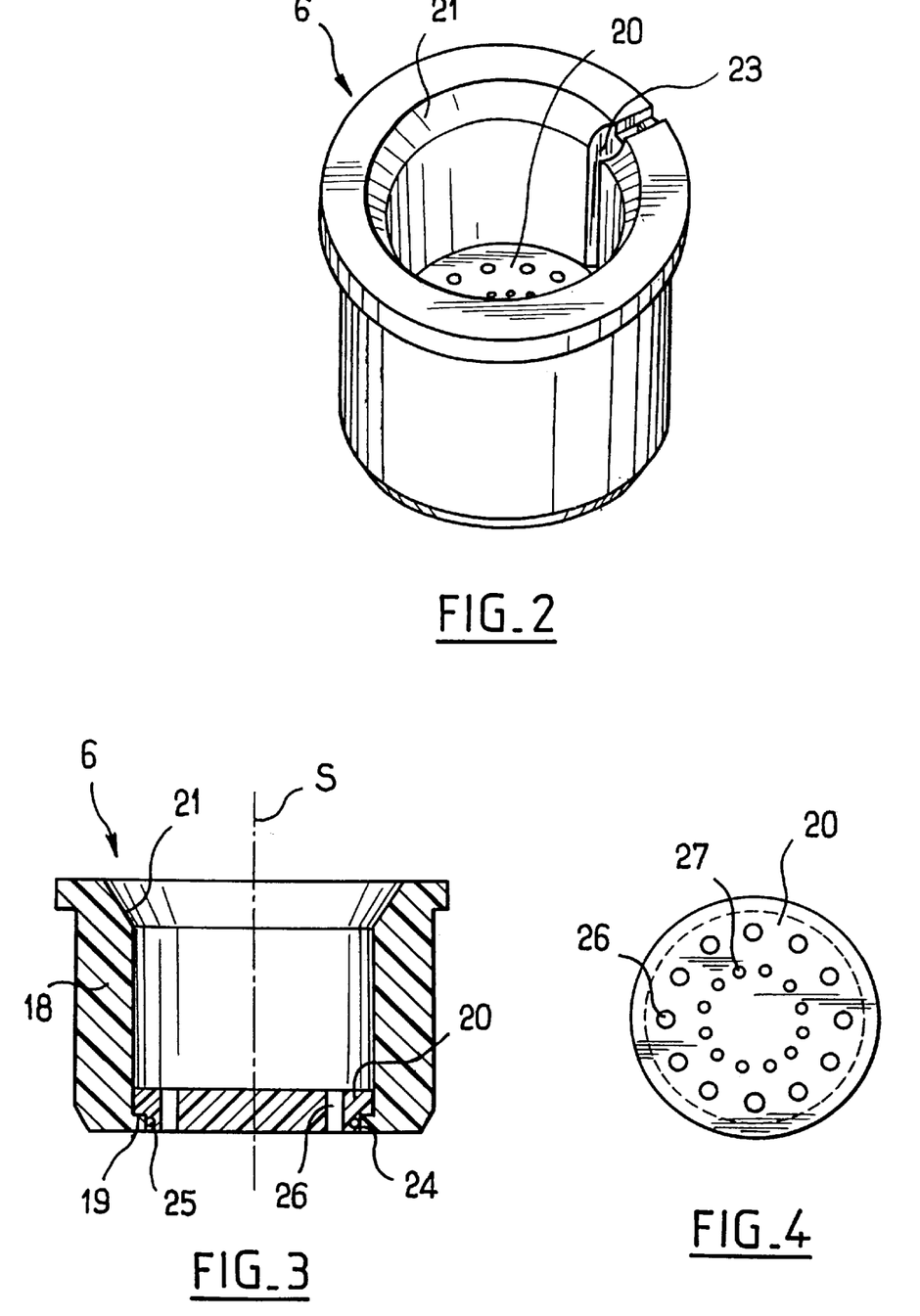
FIG. 2 is a diagrammatic perspective view of a beaker serving to contain a sample.
FIG. 3 is an axial section of the beaker shown in FIG. 2.
FIG. 4 is a view showing the bottom of the beaker as seen from above.

FIGS. 2 and 3 show a beaker 6 in isolation.

The beaker comprises a body 18 that is generally circularly symmetrical about an axis of symmetry S. The bottom portion 19 of the body has a shoulder that serves as a seat for a shouldered part 20 constituting the bottom of the beaker 6. The inside surface of the body 18 is circularly cylindrical over the major fraction of its height and it flares at its top end to facilitate insertion of the part 20 into the body 18 through the top thereof during assembly.

Preferably, as shown in FIG. 2, the body 18 is internally grooved over a portion of its height starting from its top end to form a housing 23 that is intended, when the sample is a lock of hair having a collar clamped therearound, to receive the collar in order to hold the lock of hair more securely inside the beaker 6, and in particular prevent it from rotating about the axis S.

As can be seen on examining FIG. 3, the bottom portion of the part 20 which fits in the bottom opening 24 of the body 18 has an annular groove serving to receive an O-ring 25 for holding the part 20 by friction in the body 18 and also for providing sealing between the part 20 and the body 18.

The part 20 is also pierced throughout its entire thickness by a series of circular-section channels parallel to the axis S and disposed in two concentric circles about the axis, as shown in FIG. 4. The outer channels, referenced 26, have a through section of diameter that is greater than that of the inner channels. This particular disposition makes it possible to locate the drying gas flow passing through the part 20 mainly along the inside surface of the body 18 against which the sample tends to press when the sample is constituted by a lock of hair forming a loop inside the beaker 6.

Figure 5:
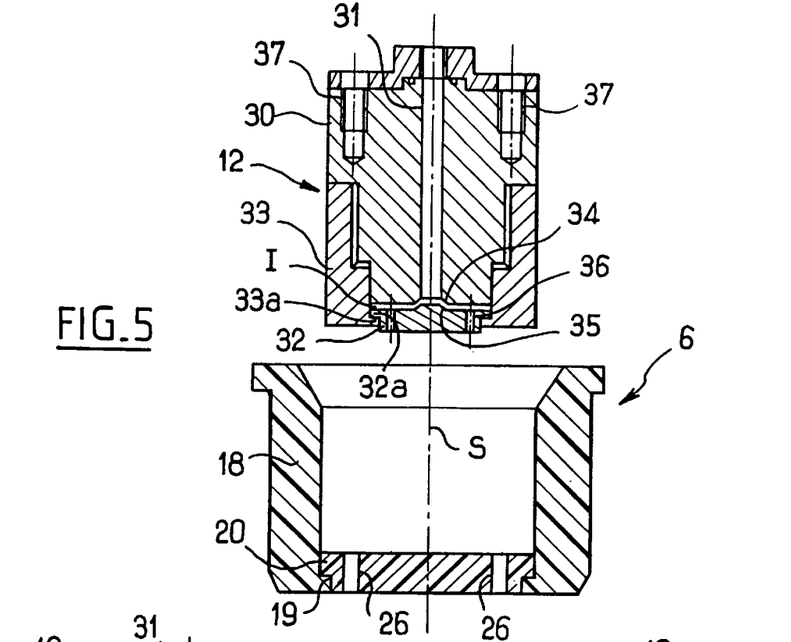
FIG. 5 is a diagrammatic axial section view showing a piston prior to being lowered into the corresponding beaker.

FIG. 5 shows a piston 12 held above an associated beaker 6.

The piston 12 comprises a body 30 pierced by a central bore 31 having the same axis as the axis of symmetry S of the corresponding beaker 6. A flap 32 is mounted at the bottom end of the body 30 by means of a shouldered retaining part 33 screwed to the body 30. The bore 31 opens out above the flap 32 via a conical opening 34, and the top face of the flap 32 has a frustoconical central portion 35 shaped to fit in the opening 34 and to close the bore 31 when the flap 32 is pressed against the body 30. In the vicinity of its periphery, the flap 32 is pierced by a plurality of channels 36 extending parallel to the axis S and enabling a liquid or a gas inserted into the bore 31 to escape from the bottom portion of the piston 12.

In the absence of backing pressure, the flap 32 has a rim 32a at its periphery resting on a shoulder 33a of the retaining part 33. A gap I is left between the facing faces of the body 30 and of the flap 32 enabling a liquid or gaseous fluid passing through the bottom end of the bore 31 to reach the channels 36. Tapped blind holes 37 are formed in the top portion of the body 30 to fix the piston 12 to the tray 10.

The retaining part 33 has a circularly cylindrical radially outer surface situated in correspondence with the radially outer surface of the body 30. The outside diameter of the piston 12 is smaller than the diameter of the inside surface of the body 18 of the beaker 6, so as to leave annular clearance between the beaker 6 and the piston 12 when the piston is lowered into the beaker 6.

A non-limiting example of how the above-described apparatus is implemented for the purpose of determining the fastness of hair dye is described below with reference to FIGS. 6 to 15.

Initially, a pad of foam or sponge 40 is placed in the bottom of each beaker 6 followed by a sample E, while the corresponding piston is raised.

Figure 6:
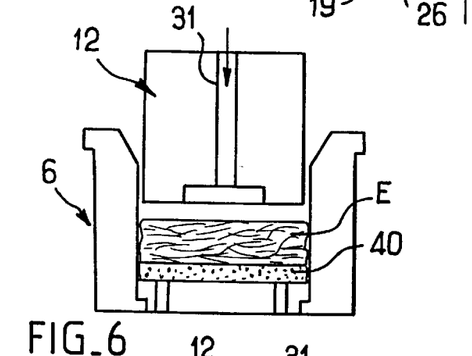
FIGS. 6 to 15 show different steps in the treatment of a sample.
Figure 7:
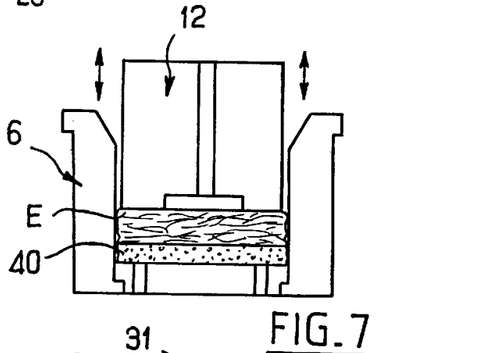

Thereafter, the piston 12 is lowered as shown in FIG. 6 and the sample E is wetted by delivering water via the bore 31. The piston 12 is then controlled by the control means 14 to move with reciprocating motion over a predetermined stroke inside the beaker 6, as shown in FIG. 7. On each down stroke of the piston 12, the flap 32 closes to prevent the liquid contained in the beaker 6 from rising up the bore 31 of the piston 12. At the bottom of its stroke, the piston 12 compresses the sample E and the pad 40 slightly, whereas at the top of its stroke, it leaves a gap relative to the top face of the sample E, thus massaging the sample E and impregnating it thoroughly. Once the sample E has been completely wetted, it is squeezed out by extending the down stroke of the piston so that excess water is expelled through the channels 26 and 27 of the part 20.

Figure 8:
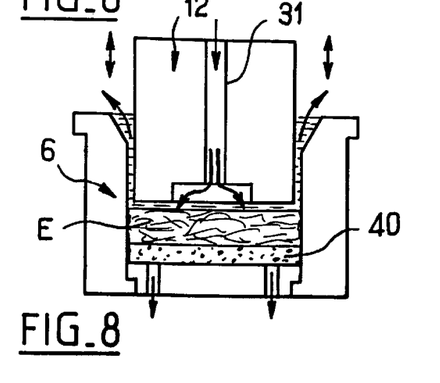

Thereafter, a predetermined quantity of dye is injected via the bore 31 and the piston 12 is again caused to move with reciprocating motion to massage the sample E and enhance the action of the dye on the fibers. The quantity of dye delivered to each beaker is preferably determined by means of a specific dispenser apparatus as described below. At the end of a predetermined length of time, the sample E is squeezed out again by lengthening the down stroke of the piston, and the sample is then rinsed by injecting rinsing water via the bore 31 while causing the piston to perform reciprocating motion to perform massaging. The rinsing water is emptied both via the channels 26 and 27 and by overflowing, as shown in FIG. 8.

After rinsing, the sample E is squeezed out by moving the piston 12 downwards. Immediately after squeezing out, it may be necessary to unstick the sample from the piston 12 while the piston is being raised by delivering a jet of compressed air through the bore 31. In addition to its effect of unsticking the sample E, the jet of compressed air also serves advantageously to purge the bore 31 and ensure that there remain no traces of dye therein before performing the following operation.

Figure 9:
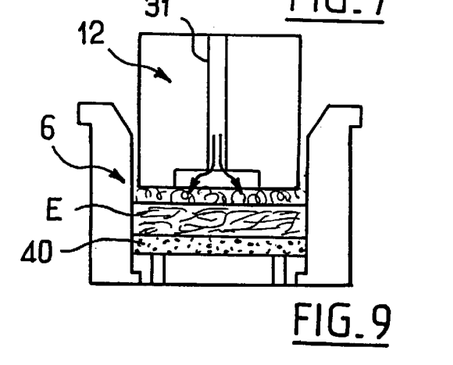
Figure 10:
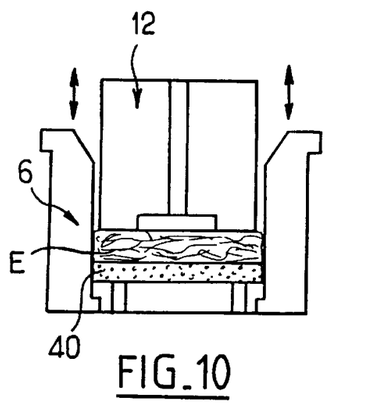

After the sample has been rinsed and squeezed out, it is possible to deliver a measured quantity of shampoo via the bore 31, as shown in FIG. 9. This quantity of shampoo is delivered into the beaker 6 by means of compressed air which advantageously causes the shampoo to foam on leaving the flap 32. After the quantity of shampoo has been dispensed, the piston 12 is caused to perform reciprocating motion, thereby massaging the sample, as shown in FIG. 10. The quantity of shampoo comes from the same dispenser apparatus as that used for measuring the quantity of dye.

Figure 11:
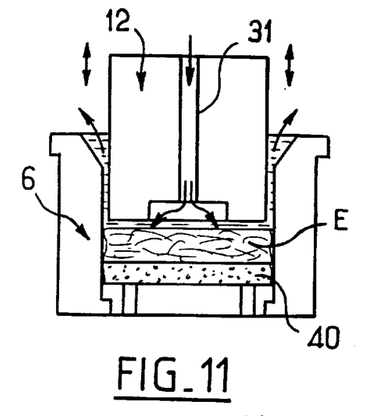
Figure 12:
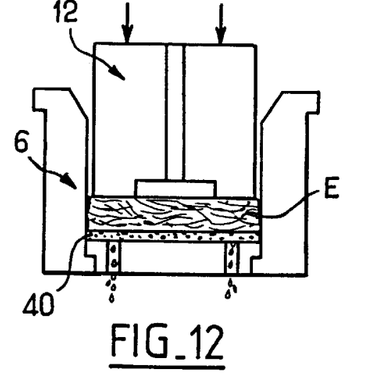

Once shampooing has been performed, the sample is rinsed by delivering rinsing water via the bore 31 while causing the piston to reciprocate so as to massage the sample, as shown in FIG. 11. Thereafter, the sample can be squeezed out by extending the down stroke of the piston 12, as shown in FIG. 12.

Heater means are preferably provided to maintain the samples E at a desired temperature while dye and shampoo are being applied thereto.

The heater means are preferably constituted by one or more heater resistances integrated in the plate 3.

This causes heat to be transmitted to each beaker 6 not uniformly over its entire height, but mainly via its bottom portion in contact with the plate 3. A temperature gradient is thus established making it possible to approximate real conditions for treating hair. Experimental conditions are thus more representative of the real conditions in which dye and shampoo are applied than is the case when dye and shampoo are maintained in uniform manner at a constant temperature by means of a water bath.

Figure 13:
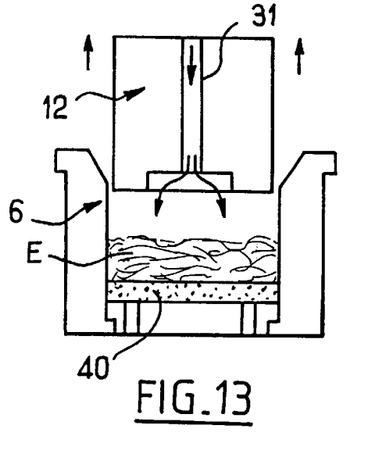

For drying purposes, the piston is raised before delivering a flow of drying air as shown in FIG. 13. It may be necessary to unstick the sample E from the bottom face of the piston 12 by delivering a jet of compressed air via the bore 31.

Figure 14:
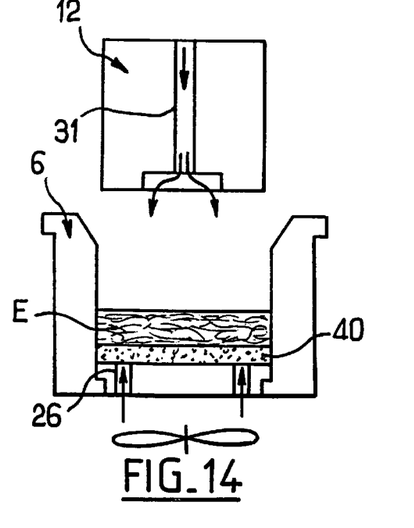
Figure 15:
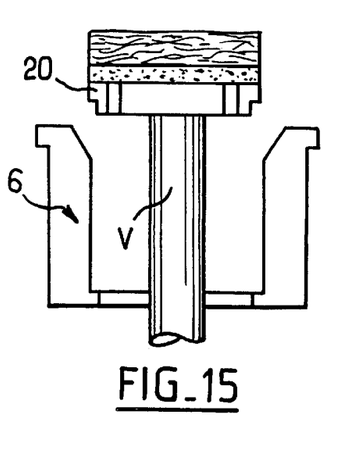

The sample is dried by delivering air, and preferably hot air via the channels 26 and 27. To reduce drying time, the sample is subjected alternately to a flow of hot air and to a flow of cold air. To do this, it is possible to vary the temperature of the air delivered by the blower, but preferably hot air is delivered continuously via the blower at substantially constant temperature while jets of cold compressed air are delivered intermittently via the bore 31, as shown in FIG. 14.

Once the sample E is dry, the treated sample can be analyzed by using a manipulator arm to take the beaker 6 to an analysis station. The part 20 is advantageously raised by means of an actuator V to remove the sample E from the beaker 6.

After the sample has been analyzed, the beaker can be put back on the plate 3 for a new treatment cycle.

With reference to FIGS. 16 to 20, there follows a description of a preferred way of bringing a measured quantity of treatment liquid into each beaker.

Figure 16:
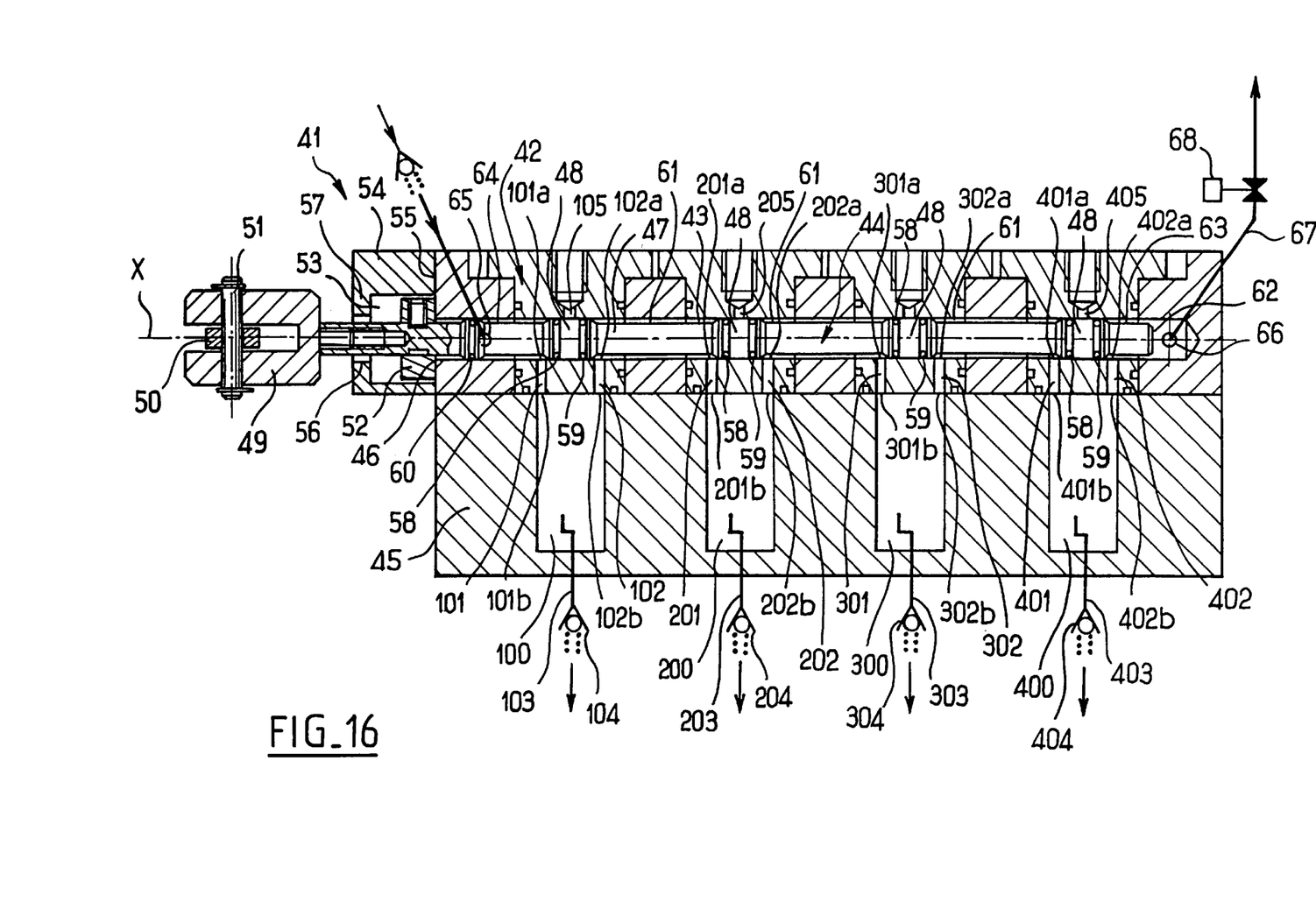
FIG. 16 is an axial section view through apparatus for dispensing predetermined quantities of a treatment liquid into the beakers.

Measured quantities of treatment substance are preferably dispensed into the beakers by means of apparatus 41 as shown in FIG. 16.

This apparatus 41 comprises a dispenser body 42 having a housing 43 slidably receiving a selector member 44 that is elongate along a longitudinal axis X. The housing 43 is circularly cylindrical about the axis X.

A block 45 is fitted beneath the dispenser body 2. A plurality of liquid-collecting chambers are formed in the block 45. In the example described, there are four such chambers and they are given respective references 100, 200, 300, and 400. These chambers are of a volume that corresponds to the quantity of substance to be delivered to each of four beakers when each chamber dispenses its content into a respective beaker, or else to more than four beakers when the content of a chamber is shared between a plurality of beakers in a group of beakers. It is assumed below that the content of a chamber is delivered to a single beaker associated with the chamber.

Figure 17:
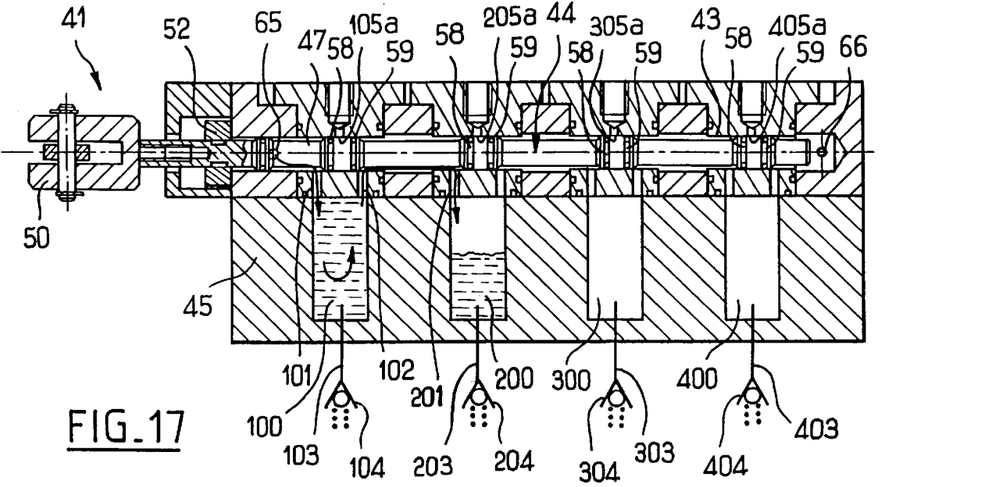
FIGS. 17 to 19 show the FIG. 16 apparatus during different steps of its operation.
Figure 18:
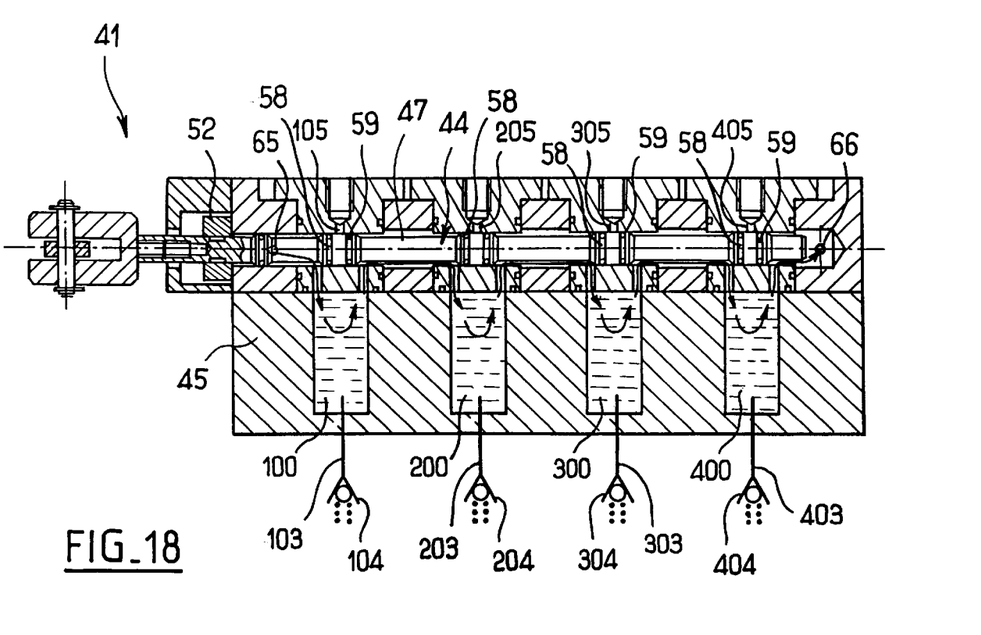
Figure 19:
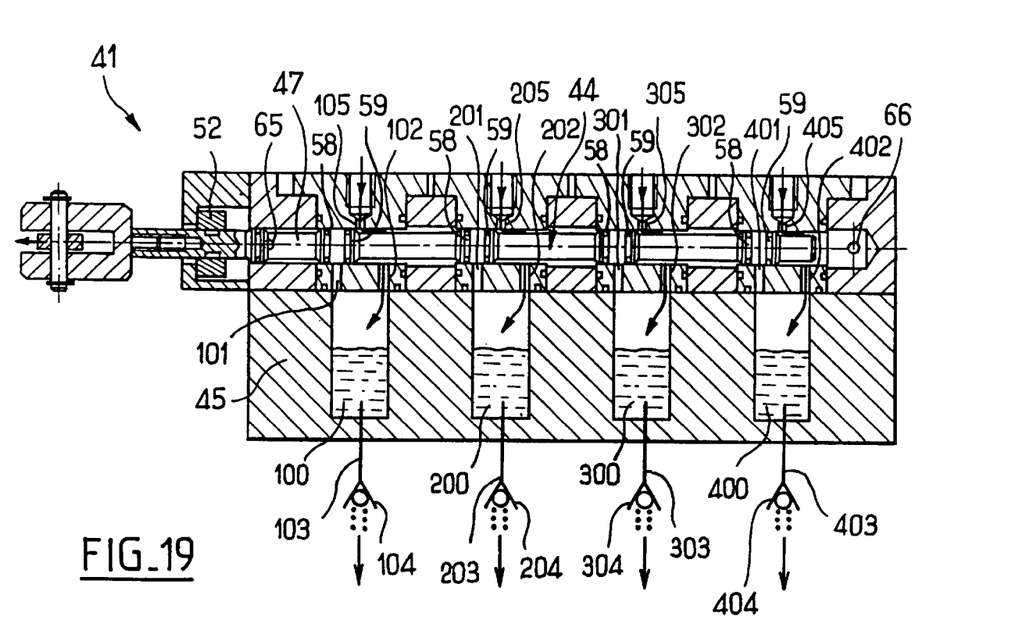

The housing 43 is open at one end 46 situated on the left in the figures, and the selector member 44 extends beyond the body of the dispenser 42 at said end. The selector member 44 comprises a rod 47 partially engaged in the housing 43 and having spaced-apart portions 48 along its length that are of circular right section adapted for sliding in the housing 43. The end of the rod 47 situated outside the housing 43 is secured to a fork 49 connected to an arm 50 in hinged manner about an axle 51. The arm 50 can be rotated about an axis perpendicular to the axis X and parallel to the section plane of FIG. 16 so as move the selector member 44 parallel to the axis X, between a position for filling the chambers 100, 200, 300, and 400, as shown in FIGS. 16 to 18, and a position for dispensing the contents of said chambers, as shown in FIG. 19.

A collar 52 is fixed to the rod 47 outside the housing 43 and moves in a housing 53, which housing is formed by fitting a part 54 against the face 55 of the dispenser body 42 through which the rod 47 projects. A hole 56 is formed in the end wall 57 of said housing 53 to pass the portion of the rod 47 which is connected to the fork 49.

When the selector member 44 is in said filling position, the collar 52 comes into abutment against the face 55, and when the selector member 44 is in said dispensing position, the collar 52 comes into abutment against the end wall 57 of the housing 53.

Each chamber 100, . . . , 400 communicates with the housing 43 via a pair of channels 101 & 102, . . . , 401 & 402. These channels 101 & 102, . . . , 401 & 402 are constituted by holes through the dispenser body 42, having axes perpendicular to the axis X and extending parallel to the section plane of FIG. 16.

The channels 101, 201, 301, and 401 are referred to as "inlet" channels while the channels 102, 202, 302, and 402 are referred to as "outlet" channels.

References 101*a* & 102*a*, . . . , 401*a* & 402*a* designate the orifices through which the channels 101 & 102, 401 & 402 open out respectively into the housing 43, and references 101*b* & 102*b*, . . . , 401*b* & 402*b* designate the orifices whereby the channels 101 & 102, . . . , 401 & 402 open out into the chambers 100, . . . , 400.

Each chamber 100, . . . , 400 communicates with a liquid dispenser pipe opening out into the bores 31 of the pistons 12. To clarify the drawing, the pipes 103, . . . , 403 associated with said chambers are shown very diagrammatically.

Each pipe 103, . . . , 403 is provided with a valve that opens when the pressure of the liquid contained in the corresponding chamber exceeds a predetermined value. The valves associated with pipes 103, . . . , 403 are given respective references 104, . . . , 404.

Each valve is advantageously fixed on a part (not shown) which makes it possible, by adjusting its position, to modify the internal volume of the associated liquid-collecting chamber, and thus the quantity of liquid that is dispensed through the valve.

Channels are provided in the dispenser body 42 to enable compressed air to be brought into each chamber 100, . . . , 400 to force the liquid contained in said chamber to be expelled via the associated dispensing pipe 103, . . . , 403. References 105, . . . , 405 designate the compressed air feed channels. The channels 105, . . . , 405 open out via respective ends 105*a*, . . . , 405*a* into the housing 43 and via opposite ends into the bottoms of tapped holes for receiving connection endpieces that are connected to a pipe which is itself connected to a source of compressed air.

On examining FIG. 16, it will be observed that the axes of the channels 105, . . . , 405 are parallel with the axes of the channels 101 & 102, . . . , 401 & 402, and that for a given chamber, the axis of the compressed air feed channel is equidistant between the associated inlet and outlet channels. Thus, in the case of chamber 100, for example, the axis of channel 105 is equidistant between the inlet channel 101 and the outlet channel 102. The same applies to chambers 200, 300, and 400.

On each portion 48 of the rod 47 there are formed two annular grooves in which there are received two O-rings. Reference 58 designates the O-ring situated adjacent to the end 46 of the housing 43 and reference 59 designates the O-ring situated closer to the opposite end. Each O-ring 58 or 59 is interposed radially between the rod 47 and the wall of the housing 43.

The rod 47 also includes, between the collar 52 and the adjacent portion 48, an annular groove for receiving an O-ring 60 interposed radially between the rod 47 and the wall of the housing 43.

Between the portions 48, the rod 47 is of narrowed circular section so as to leave an annular gap 61 relative to the wall of the housing 43. The same applies between the portion 47 situated furthest from the end 46 of the housing 43 and the free end 62 of the rod 47 and between the annular groove formed to receive the O-ring 60 and the portion 48 closest to the end 46 of the housing 43. Respective annular gaps are thus formed given referenced 63 and 64.

Orifices 65 and 66 open out into the housing 43 respectively to feed the liquid which is to fill the liquid-collecting chambers 100, . . . , 400 and to allow liquid to be removed when all of the chambers 100, . . . , 400 have been filled. The orifice 66 opens out at the end of the housing 43 and communicates with a pipe 67 which is provided with a valve 68 in the embodiment described.

When the rod 47 is in the filing position, i.e. when the collar 52 bears against the face 55, the orifice 65 is situated between the O-ring 60 and the O-ring 58 of the portion 48 of the rod 47 adjacent to the end 46 of the housing 43. The O-ring 60 thus prevents liquid from leaving the housing 43 via the end 46.

When the selector member 44 is in the filling position, each pair of O-rings 58 & 59 associated with each portion 48 is situated on either side of a compressed air feed channel, thereby isolating it. The O-rings 58 & 59 are also situated between the pairs of channels 101 & 102, . . . , 401 & 402 associated with the chambers 100, . . . , 400 so as to force the filling liquid coming from the orifice 65 to pass in succession through the chambers 100, . . . , 400 as explained below.

When the selector member 44 is moved to the left of FIG. 16 so as to occupy the dispensing position, corresponding to FIG. 19, then the pairs of O-rings 58 & 59 are situated respectively on either side of the inlet channels 101, . . . , 401 to isolate the orifices 101a, . . . , 401a. Also, each compressed air feed channel 105, . . . , 405 opens out level with an O-ring 59 so that the compressed air feed orifices 105a, . . . , 405a are no longer isolated from the housing 43 when the selector member 44 is in this position.

The apparatus 41 operates as follows.

To fill the chambers 100, . . . , 400 the selector member 44 is moved into its filling position, i.e. it is moved fully to the right as shown in FIGS. 16 to 19, its collar 52 coming into abutment against the face 55. The source of compressed air is isolated from the channels 105, . . . , 405 by an electrically controlled valve in the closed state (not shown in the figures). The liquid which leaves via the orifice 65 flows into the annular gap 64 and then via the inlet channel 101 into the first liquid-collecting chamber 100 because of the presence of the first O-ring 58 (starting from the left of FIG. 16). Once the chamber 100 has been filled, the liquid overflows via outlet channel 101 and penetrates into the annular clearance 61 defined axially by the first O-ring 59 and by the second O-ring 58. The liquid enters into the second chamber 200 via its inlet channel 201, and once the second chamber has been filled, it overflows via the outlet channel 202. The liquid thus reaches the third chamber via the annular clearance 61, defined axially by the second O-ring 59 and the third O-ring 58. When this chamber has been filled, the liquid overflows via its outlet channel 302 to reach the annular clearance 61 formed between the third O-ring 59 and the fourth O-ring 58. The liquid penetrates the last chamber 400 via its inlet channel 401 and once it has been completely filled it overflows via outlet channel 402 to reach orifice 66 and be removed via pipe 67, valve 68 then being open. The valves 104, 204, . . . , 404 remain closed during the filling stage, with the pressure of the liquid being lower than the pressure at which the valves open. Once all of the chambers 100, . . . , 400 have been filled, the selector member 44 is moved to the left in FIG. 19, so that the collar 52 comes into abutment against the end wall 57 of the housing 53. The valve which previously isolated the channels 105, . . . , 405 from the compressed air feed is opened. The valve 68 is closed. The pairs of O-rings 58 & 59 no longer isolate the orifices 105a, . . . , 405a, but now isolate the inlet channels 101, . . . , 401. The orifice 65 is isolated by the O-ring 60 and the first O-ring 58. In this position of the selector member 44, the orifices 105a, . . . , 405a communicate with the respective outlet channels 102, . . . , 402. The pressure of the compressed air is greater than the pressure at which the valves 104, . . . , 404 open, and as a result the liquid contained in each chamber is expelled through the corresponding valve to the associated piston 12.

Figure 20:
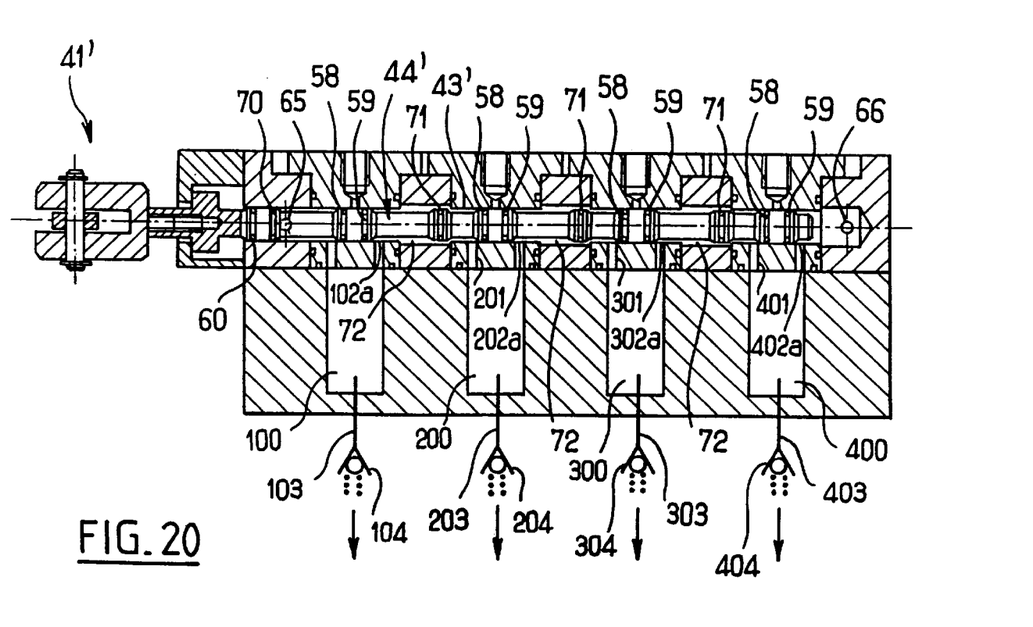
FIG. 20 shows a variant embodiment of the apparatus shown in FIGS. 16 to 19.

FIG. 20 shows a variant embodiment 41' which differs mainly from the above-described embodiment by the presence of additional O-rings. The same numerical references are used in this figure to designate elements that are identical or functionally analogous, and they are therefore not described again in detail.

The selector member, now referenced 44', carries an additional O-ring 70 between the O-ring 60 and the first O-ring 58. This O-ring 70 is situated on the selector member 44' in such a manner that when it is in the filling position, corresponding to FIG. 20, the liquid feed orifice 65 opens into the housing 43' between the O-ring 70 and the first O-ring 58, whereas when the selector member 44' is in the dispensing position, the orifice 65 is isolated between the O-rings 60 and 70.

The selector member 44' also carries three additional O-rings 71 each situated between an O-ring 59 and the following O-ring 58. Annular recesses 72 are formed in the housing 43' so as to leave a gap between each O-ring 71 and the wall of the housing 43' when the selector member 44' is in the filling position. This prevents the O-rings 71 closing the passage for liquid from one chamber to the following chamber during filling. When the selector member 44' is in the filling position, the O-rings 71 are situated close to the right ends of the recesses 72 such that when the selector member 44' is moved to the right into the dispensing position, the three O-rings 71 bear against the wall of the housing 43' situated between the recesses 72 and the channels 201, 301, and 401 respectively. The stroke of the selector member 44' to the right is selected in such a manner that the orifices 102a, 202a, 302a, and 402a are isolated by each pair of O-rings 58 & 59 when the selector member 44' is in the dispensing position. For the chamber 100, compressed air passes via the annular clearance defined axially by the O-ring 70 and the first O-ring 58, whereas for the chambers 200, . . . , 400, the compressed air passes via the annular clearance formed between an O-ring 71 and the immediately following O-ring 58, going from left to right in FIG. 20. The orifice 66 is isolated by the last O-ring 59 when the selector member 44' is in the dispensing position, so it is no longer necessary to provide for an electrically controlled valve to close the emptying pipe.

The invention is advantageously used for determining the fastness of hair dye, as mentioned above. Nevertheless, it would not go beyond the ambit of the invention to treat fibers other than hair, e.g. metal fibers or synthetic fibers.

What is claimed is:

1. Apparatus for implementing successive treatment on samples, the apparatus comprising:

a plurality of beakers each adapted to receive a sample;

feed means for feeding at least one treatment liquid into each beaker;

flow establishing means for establishing a flow of drying gas in each beaker; and a plurality of pistons associated with respective ones of said beakers and drive means for driving said pistons within said beakers.

2. The apparatus according to claim 1, further comprising control means for controlling said drive means so as to control displacement of said pistons inside said beakers in a first mode of operation to have reciprocating motion over a predetermined stroke to apply a massaging action to the samples, and in a second mode of operation to have a downward motion over a greater stroke to perform a squeezing-out action on the samples.

3. The apparatus according to claim 1, wherein each piston has at least one treatment liquid feed channel for the corresponding beaker passing therethrough.

4. The apparatus according to claim 3, wherein each piston is fitted with a flap for preventing treatment liquid from moving back into said at least one feed channel when the piston moves down into the corresponding beaker.

5. The apparatus according to claim 4, wherein each piston has a body, and wherein said flap is retained at the bottom end of said body, said body being movable between a position in which it closes said channel and a position in which it enables said treatment liquid to flow through orifices in said flap.

6. Apparatus for implementing successive treatments on samples, the apparatus comprising:

a plurality of beakers each adapted to receive a sample;

feed means for feeding at least one treatment liquid into each beaker;

flow establishing means for establishing a flow of drying gas in each beaker; and wherein the bottom of each beaker is pierced by orifices and wherein the apparatus includes means for delivering a flow of drying gas into each beaker via said orifices.

7. The apparatus according to claim 6, further including means for selectively putting said orifices into communication either with an emptying pipe or with a blower.

8. the apparatus according to claim 6, wherein said orifices are disposed in two concentric rows in the bottom of each beaker with the flow section of the orifices situated at the periphery being greater than the flow section of the orifices situated in the center.

9. Apparatus for implementing successive treatments on samples, the apparatus comprising:

a plurality of beakers each adapted to receive a sample;

feed means for feeding at least one treatment liquid into each beaker;

flow establishing means for establishing a flow of drying gas in each beaker; and wherein the bottom of each beaker is removable and capable of being moved upwards inside the beaker.

10. Apparatus for implementing successive treatments on samples, the apparatus comprising:

a plurality of beakers each adapted to receive a sample;

feed means for feeding at least one treatment liquid into each beaker;

flow establishing means for establishing a flow of drying gas in each beaker; and wherein each beaker has an inside groove for preventing the sample from rotating inside the beaker.

11. Apparatus for implementing successive treatments on samples, the apparatus comprising:

a plurality of beakers each adapted to receive a sample;

feed means for feeding at least one treatment liquid into each beaker;

flow establishing means for establishing a flow of drying gas in each beaker; and a foam or sponge pad on the bottom of each beaker.

12. Apparatus for implementing successive treatments on samples, the apparatus comprising:

a plurality of beakers each adapted to receive a sample;

feed means for feeding at least one treatment liquid into each beaker;

flow establishing means for establishing a flow of drying gas in each beaker;

a dispenser body having a housing into which there opens at least one feed inlet for said liquid;

a succession of liquid collecting chambers communicating via respective inlet orifices and outlet orifices with said housing, and further communicating with the outside via respective liquid dispensing outlets, each of said outlets being provided with closure means capable of being opened to dispense the liquid in the corresponding beaker;

respective expulsion gas feed channels associated with said chambers;

a selector member movable in said housing between a filling position and a dispensing position; and sealing means placed in said housing between the body of the dispenser and said selector member, said body and selector member being shaped and said sealing means being position such that when said selector member is in the filling position, said sealing means defines liquid passages in said housing between an outlet orifice of one chamber and inlet orifice of the following chamber to force circulation of the liquid from said feed inlet for said liquid through the various chambers in succession, and when said selector member is in the dispensing position, said sealing means closes said passages so as to make it possible when said closure means associated with each chamber are open, for the liquid contained within each chamber to flow out via the corresponding liquid dispensing outlet under a force from said expulsion gas.

13. The apparatus according to claim 12, wherein said expulsion gas feed channels open out into said housing and are isolated by said sealing means when the selector member is in the filling position.

14. The apparatus according to claim 12, wherein said expulsion gas comes from a source of compressed air.

15. The apparatus according to claim 12, wherein said sealing means are carried by the selector member.

16. The apparatus according to claim 12, wherein said selector member is elongate in shape and can slide inside said housing.

17. The apparatus according to claim 12, wherein each expulsion gas feed orifice is situated along the path of the selector member between the inlet orifice and the outlet orifice of a liquid-collecting chamber opening out into said housing.

18. The apparatus according to claim 12, wherein said closure means are constituted by valves that open when the pressure of the liquid in the associated liquid-collecting chamber exceeds a predetermined value.

19. The apparatus according to claim 18, wherein the volume of each liquid-collecting chamber is adjustable by moving a part carrying the associated valve.

* * * * *